United States Patent [19]

Mase et al.

[11] 4,407,704

[45] Oct. 4, 1983

[54] OXYGEN CONCENTRATION DETECTOR AND A METHOD OF DETECTING OXYGEN CONCENTRATION

[75] Inventors: Syunzo Mase, Tobishima; Shigeo Soejima, Nagoya, both of Japan

[73] Assignee: NGK Insulators, Ltd., Nagoya, Japan

[21] Appl. No.: 210,239

[22] Filed: Nov. 25, 1980

[30] Foreign Application Priority Data

Dec. 4, 1979 [JP] Japan .............................. 54-156314
Mar. 28, 1980 [JP] Japan .............................. 55-39004

[51] Int. Cl.$^3$ ........................................ G01N 27/58
[52] U.S. Cl. .................................. 204/1 T; 204/406; 204/425
[58] Field of Search .......................... 204/195 S, 1 S; 123/489; 60/276; 324/71 R

[56] References Cited

U.S. PATENT DOCUMENTS

| 3,654,112 | 4/1972 | Beekmans et al. | 204/195 S |
|---|---|---|---|
| 4,071,817 | 1/1978 | Bahl | 204/1 T X |
| 4,145,272 | 3/1979 | Nakamura et al. | 204/195 S |
| 4,265,724 | 5/1981 | Haecker et al. | 204/195 S |

OTHER PUBLICATIONS

Bauerle, J. E. Study of Solid Electrolyte Polarization by a Complex Admittance Method, J. Phys. Chem. Solids, vol. 30, 1969, pp. 2657–2670.

Friedland, B., Wing, O., and Ash, R. "Principles of Linear Networks", McGraw-Hill, New York, 1961, p. 164.

*Primary Examiner*—G. L Kaplan
*Attorney, Agent, or Firm*—Parkhurst & Oliff

[57] ABSTRACT

In a detector to measure the oxygen concentration of a gaseous mixture such as automobile exhaust gas by using the principle of an oxygen concentration cell made of an oxygen ion conductive solid electrolyte body with electrodes mounted on opposite surfaces thereof, the inventive detector and the method use AC voltage electrode means provided on the solid electrolyte body to apply an AC voltage thereof for heating the detector.

13 Claims, 14 Drawing Figures

OXYGEN CONCENTRATION DETECTOR AND A METHOD OF DETECTING OXYGEN CONCENTRATION

BACKGROUND OF THE INVENTION

1. Field of the Invention

This invention relates to a detector and a method to accurately and quickly detect the oxygen concentration in a gaseous mixture at a comparatively low temperature with a high-speed response and a low output impedance.

2. Description of the Prior Art

To measure the oxygen concentration of the exhaust gas from an internal combustion engine or the like, an oxygen concentration detector having an oxygen ion conductive solid electrolyte body and based on the principle of an oxygen concentration cell has been used. The oxygen concentration detector of the prior art generally includes a solid electrolyte body, which is for instance made of a yttria zirconia ceramic, and electrodes made of platinum. The aforementioned oxygen concentration detector of the prior art has shortcomings in that, when the temperature of the gaseous mixture being measured is comparatively low, the catalytic activity of the platinum electrode is reduced and the electric resistance of the zirconia ceramic becomes high, resulting in an increased impedance of the oxygen concentration detector which tends to make output signals of the oxygen concentration detector suitable due to interference by noises, and that the comparatively low temperature of the gaseous mixture tends to make the response slow. As a result, the practicable lowest operative temperature of the oxygen concentration detector of the prior art has been about 350° C. On the other hand, at the starting of an internal combustion engine and during idling thereof, the temperature of the exhaust gas therefrom can be as low as 250° to 300° C., which is below the aforementioned lowest operative temperature of the prior art. Accordingly, the conventional oxygen concentration detector has a drawback of not providing satisfactory operation when the temperature of the gaseous mixture being measured is low.

SUMMARY OF THE INVENTION

Therefore, an object of the present invention is to obviate the aforesaid shortcomings and drawback of the prior art. To fulfill this object, the invention provides an oxygen concentration detector and a method of detecting oxygen concentration of a gas which detector and method ensure accurate and quick detection of the oxygen concentration with a low output impedance.

An object of the present invention is to provide an oxygen concentration detector to detect oxygen concentration of a gas, comprising an oxygen ion conductive solid electrolyte body, electrodes mounted on opposite surfaces of said solid electrolyte body so as to form an oxygen concentration cell, and AC power supplying means to heat the solid electrolyte body by flowing electric current therethrough.

Another object of the present invention is to provide an oxygen concentration detector to detect oxygen concentration of a gas, comprising an oxygen ion conductive solid electrolyte body, electrodes mounted on opposite surfaces of said solid electrode body so as to form an oxygen concentration cell, AC power supplying means having an AC power source connected to said electrodes for forming said oxygen concentration cell, means for detecting selectively DC voltage level from the terminal voltage of the detector, and means for preventing current due to DC voltage level of the terminal voltage of the detector from flowing into the AC power source, whereby the solid electrolyte body is heated by flowing electric current therethrough.

A further object of the present invention is to provide an oxygen concentration detector to detect oxygen concentration of a gas, comprising an oxygen ion conductive solid electrolyte body, electrodes mounted on opposite surfaces of said solid electrode body so as to form an oxygen concentration cell, AC power supplying means having an AC power source connected to said electrodes for forming said oxygen concentration cell, means for detecting selectively DC voltage level from the terminal voltage of the detector, means for preventing current due to DC voltage level of terminal voltage of the detector from flowing into the AC power source, and means for separating a circuit connected to AC power source from the terminal of the oxygen concentration detector, whereby the solid electrolyte body is heated by flowing electric current therethrough.

A still further object of the present invention is to provide an oxygen concentration detector to detect oxygen concentration of a gas, comprising an oxygen ion conductive solid electrolyte body, electrodes mounted on opposite surfaces of said solid electrode body so as to form an oxygen concentration cell, an AC power supplying means having at least one AC voltage electrode separated from said electrodes provided on said solid electrolyte body for forming said oxygen concentration cell and an AC power source connected to said AC voltage electrode, means for detecting selectively DC voltage level from terminal voltage of the detector, and means for preventing current due to DC voltage level of terminal voltage of the detector from flowing into the AC power source, means for separating a circuit connected to the AC power source from the terminal of the oxygen concentration detector, whereby the solid electrolyte body is heated by flowing electric current therethrough.

Another object of the present invention is to provide an oxygen concentration detector to detect oxygen concentration of a gas, comprising an oxygen ion conductive solid electrolyte body, electrodes mounted on opposite surfaces of said solid electrode body so as to form an oxygen concentration cell, and AC electrode means provided on said solid electrolyte body, said AC electrode means being adapted to receive an AC voltage to cause an AC current to flow through said solid electrolyte body.

Another object of the present invention is to provide a method of detecting oxygen concentration by detecting oxygen partial pressure of a gas, comprising steps of forming an oxygen concentration cell by mounting electrodes on opposite surfaces of an oxygen ion conductive solid electrolyte body, applying an AC voltage to said solid electrolyte body so as to generate heat in said solid electrolyte body, and measuring a voltage across said electrodes under the thus heated conditions, whereby said voltage across said electrodes representing oxygen concentration is detected.

Another object of the present invention is to provide a method of detecting oxygen concentration by detecting oxygen partial pressure of a gas, comprising steps of forming an oxygen concentration cell by mounting electrodes on opposite surfaces of an oxygen ion conductive solid electrolyte body, applying an AC voltage to said solid electrolyte body so as to generate heat in said solid electrolyte body, and measuring a voltage across said electrodes under the thus heated conditions, said voltage across said electrodes representing oxygen concentration being detected, wherein said AC voltage applied to said solid electrolyte body has the frequency which causes an AC polarization of said oxygen concentration cell mostly as polarization which is due to electric resistances of crystal grains of said solid electrolyte body.

More particularly, according to the present invention, if the temperature of the gas being measured, such as engine exhaust gas, is too low to ensure satisfactory operation of an oxygen concentration detector, an AC voltage, preferably a high-frequency AC voltage, is applied to the solid electrolyte body constituting the oxygen concentration detector so as to cause an electric current to flow therethrough, whereby heat is generated in the solid electrolyte body until the thus generated heat raises the temperature of the solid electrolyte body and the electrode provided on the surface of the solid electrolyte to a sufficiently high temperature to ensure normal operation thereof. Accordingly, even when it is exposed to a gas of comparatively low temperature, the oxygen concentration detector of the invention operates properly.

BRIEF DESCRIPTION OF THE DRAWINGS

For a better understanding of the invention, reference is made to the accompanying drawings, in which.

Like parts are designated by like numerals and symbols throughout different views of the drawings.

DESCRIPTION OF THE PREFERRED EMBODIMENTS

Figure 1:
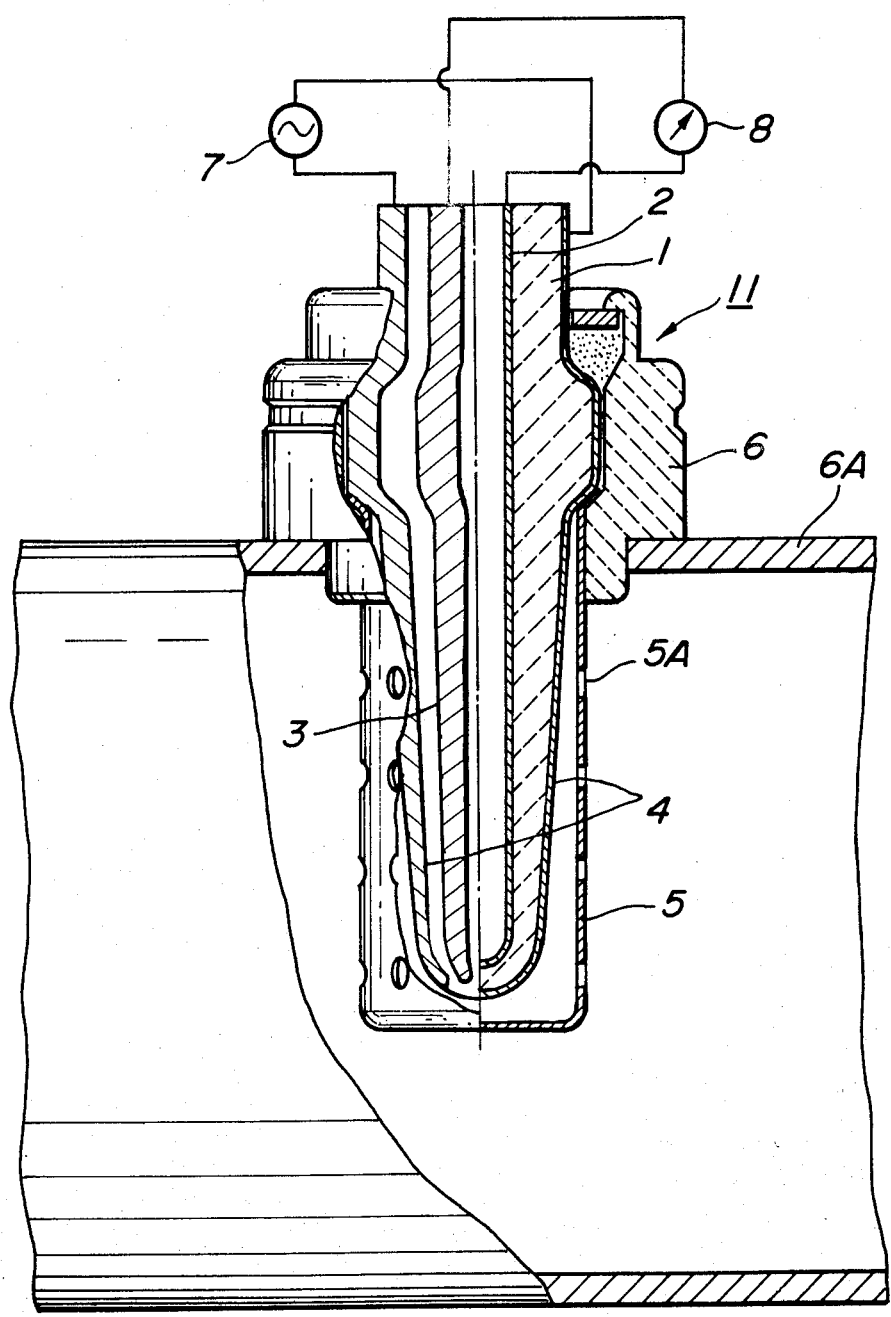
FIG. 1 is a schematic sectional view of an embodiment of the oxygen concentration detector according to the present invention.

Referring to FIG. 1 showing an oxygen concentration detector 11 according to the present invention, a tubular solid electrolyte body 1 has a closed end and is made of, for instance, yttria-zirconia ceramic. An inner electrode 2 made of platinum is provided on the inner surface of the tubular solid electrolyte body 1, while a plurality of outer electrodes 3 and a plurality of AC voltage electrodes 4 are alternately provided on the outer surface of the tubular solid electrolyte body 1. The solid electrolyte body 1, the inner electrode 2, and the outer electrodes 3 constitute an oxygen concentration cell. The outer electrodes 3 on the outer surface of the solid electrolyte body 1 are all electrically connected to each other and kept at the same potential. All the AC voltage electrodes 4 may be connected to one terminal of an AC power source as shown in FIG. 4 or an AC voltage may be applied across separate AC electrodes 4 as shown in FIGS. 2 and 3.

Preferably, a porous protective layer (not shown) covers that portion of the oxygen concentration detector which is exposed to an exhaust gas, as in the case of oxygen detectors of the prior art. The tip portion of the solid electrolyte body 1 is surrounded by a metal cover 5 having gas inlet openings 5A. The oxygen concentration detector is airtightly sealed in a metal housing 6 in such a manner that, when the metal housing 6 is airtightly mounted on an exhaust gas passage wall 6A, the outer surface of the tip portion of the solid electrolyte body 1 with the electrodes 3 and 4 is exposed to the exhaust gas but the exhaust gas does not leak to the inside of the solid electrolyte body or to the outside of the exhaust gas passage.

The manner in which various electrodes are mounted on the oxygen concentration detector will be now explained. Referring to an enlarged partial sectional view of FIG. 2, the inner electrode 2 is preferably mounted on the entire inner surface of the tubular solid electrolyte body 1. The outer electrodes 3 and the AC voltage electrodes 4 are alternately mounted on the outer surface of the tubular solid electrolyte body 1. The outer electrodes 3 are all kept at the same potential. In the example of FIG. 2, an AC voltage is applied across separate AC voltage electrodes. It is also possible to keep all the AC electrodes 4 at the same potential, as in the example of FIG. 4, while using the inner electrode 2 both as one concentration cell electrode and as another AC voltage electrode so as to apply an AC voltage across the inner electrode 2 and the AC voltage electrodes 4. The AC voltage is provided from an AC power source 7, and the DC voltage across the inner electrode 2 and the outer electrodes 3 is measured by a DC voltage detector 8.

Figure 2:
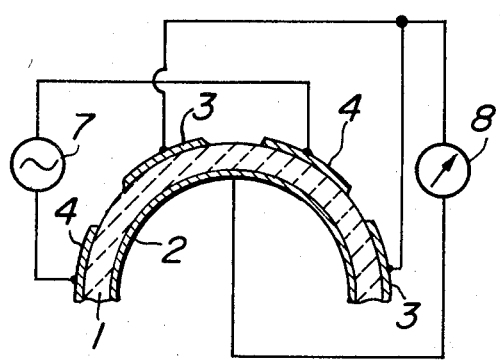
FIGS. 2 through 7 are schematic partial sectional views showing different modifications of the structure to mount electrodes on the oxygen concentration detector of the invention.
Figure 3:
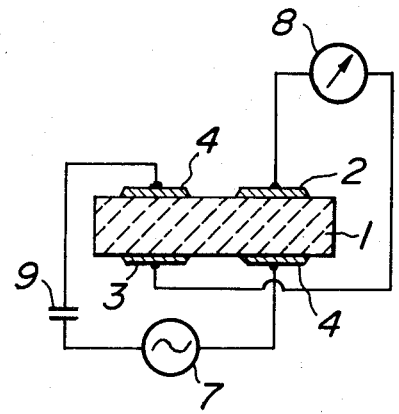
Figure 4:
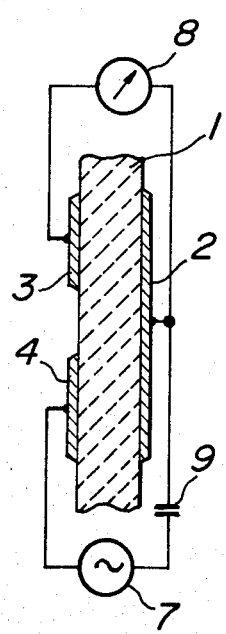

The disposition of the electrodes is not restricted to that of FIGS. 1 and 2, but many other dispositions are possible such as those shown in FIGS. 3 and 4. The AC voltage electrodes 4 may be mounted all on either surface of the solid electrolyte body 1, or on both the inner and outer surfaces of the solid electrolyte body 1.

Figure 5:
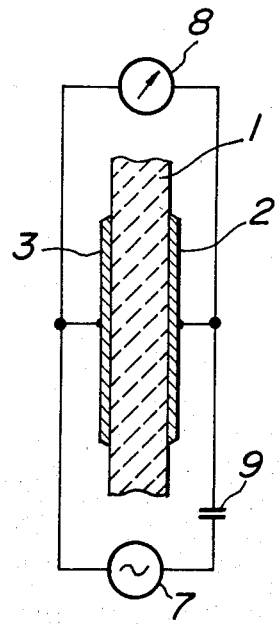
Figure 6:
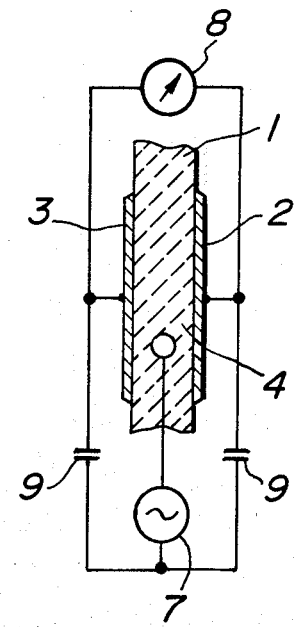
Figure 7:
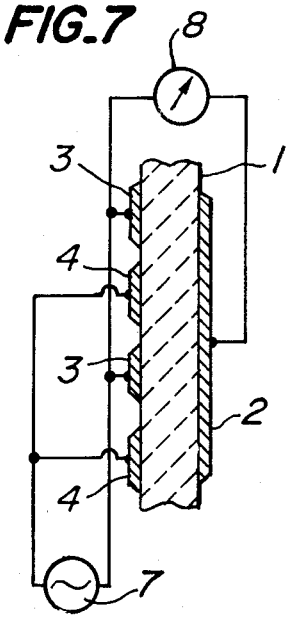

In FIGS. 3 through 6, the AC power source 7 is connected in series to a capacitor 9. Although the example of FIGS. 1 through 4 uses AC electrodes 4 separate from the external electrodes 3, the example of FIG. 5 applies an AC voltage across the inner electrode 2 and the outer electrodes 3, which electrodes 3 also act as AC voltage electrode means. In the example of FIG. 6, the AC voltage electrodes 4 (only one electrode 4 is shown) are embedded in a solid electrolyte body 1, and one end of an AC power source 7 is connected to the AC voltage electrodes 4 while the opposite end of the AC power source 7 is connected to the inner and outer electrodes 2 and 3 in parallel. In the example of FIG. 7, the AC voltage electrodes 4 are mounted on the same side of the solid electrolyte body 1 with the outer electrodes 3, and one end of the AC power source 7 is connected to the AC voltage electrodes 4 while the opposite end of the AC power source 7 is connected to the outer electrodes 3. In the embodiment of FIG. 4, the inner electrode 2 fulfills the function of the AC voltage electrode, while in the embodiment of FIGS. 5 and 6, the inner and outer electrodes 2 and 3 fulfil the function of the AC voltage electrodes, and in the embodiment of FIG. 7, the outer electrodes 3 fulfil the function of the AC voltage electrodes.

Figure 8:
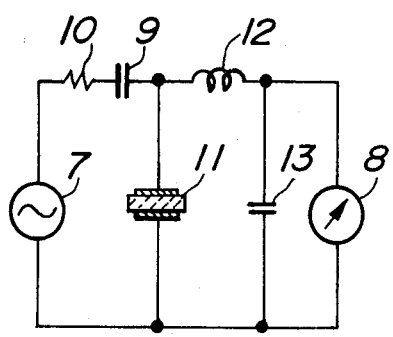
FIGS. 8 through 10 are electric circuit diagram illustrating different ways to apply an AC voltage to the oxygen concentration detector according to the present invention.
Figure 9:
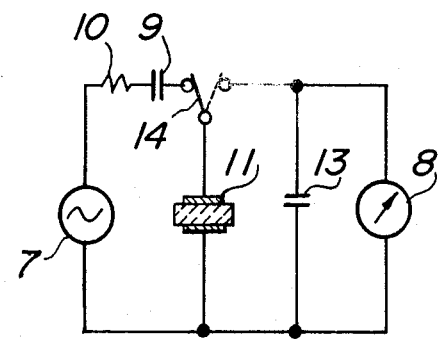
Figure 10:
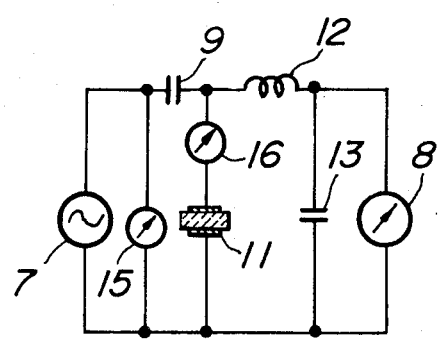

FIGS. 8 through 10 show electric circuits to apply the AC voltage from the AC power source 7 to the oxygen concentration detector 11 and to measure a DC output voltage from the oxygen concentration detector 11. The DC output voltage is an electromotive force of the oxygen concentration cell consisting of the solid electrolyte body 1 and the inner and outer electrodes 2 and 3 exposed to gases with different oxygen concentrations. In the case of the circuit of FIG. 8, the capacitor 9 prevents the DC output current of the oxygen concentration detector 11 from flowing into the AC power source 7, while permitting the AC current from the AC power source 7 to flow into the oxygen concentration detector 11 through a current limiting resistor 10. The AC current acts to heat the oxygen concentration detector 11. A choke coil 12 and a capacitor 13 form a filter circuit which eliminates AC voltages, so that the DC voltage detector 8 measures the DC output voltage from the oxygen concentration detector 11 to detect the oxygen concentration of the gas being measured.

The current limiting resistor 10 acts to prevent any excessive current from flowing through the oxygen concentration detector 11 and to minimize the AC power being applied to the oxygen concentration detector 11 when the detector 11 is sufficiently warm for effecting satisfactory detection without any substantial heating by the AC current. The continuous application of the AC voltage in the example of FIG. 8 can be replaced by intermittent application as shown in FIG. 9, wherein a switch 14 changes over the AC voltage application and the detection of the DC output voltage alternately. The AC voltage may be applied to the oxygen concentration detector 11 only when the detector 11 is too cold for satisfactory detection. In the circuit of FIG. 10, an AC voltmeter 15 and an AC ammeter 16 are provided to check the voltage of the AC power source 7 and the AC current flowing through the oxygen concentration detector 11 respectively.

In the present invention, the oxygen concentration detector 11 is heated by the heat generated in the solid electrolyte body 1 by application of an AC voltage thereto, without causing any adverse effects on the electromotive force (DC voltage) across the inner and outer electrodes 2 and 3 mounted on opposite surfaces of the solid electrolyte body 1, which electromotive force represents the oxygen concentration of the gas being measured. The reason for the successful heating with the AC voltage without affecting the DC output appears to be as follows. There is a linear relationship between the electrode potential and the amount of electrolytic products at the boundary between the electrode and the solid electrolyte body, provided that the amount of the electrolytic products is within a certain limit. If the amount of electrolytic products produced by the quantity of electricity during one half cycle of an AC current causing reactions at the electrode is within the aforementioned certain limit, the entire amount of the electrolytic products generated in one half cycle of the AC current are properly removed during the following half cycle of the opposite polarity. Thus, even if a comparatively high AC voltage, e.g., several tens of volts, is applied to the oxygen concentration detector, the quantity of electricity during one half cycle thereof can be limited to a value below a certain limit by increasing the frequency thereof, so that no adverse effects are caused on the DC output voltage of the oxygen concentration detector and no deterioration of the solid electrolyte body is caused. Accordingly, a comparatively high AC voltage can be applied to the oxygen concentration detector to heat it.

Figure 11:
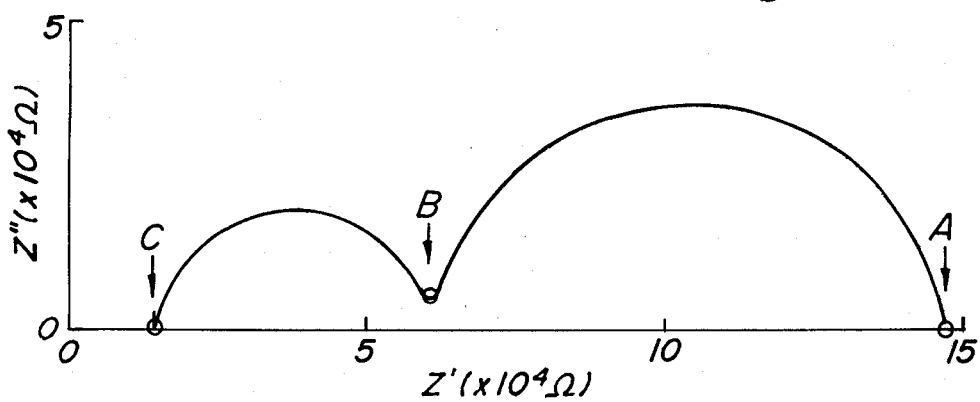
FIG. 11 is a graph showing the complex impedance characteristics of an oxygen concentration cell which is used in the method of detecting oxygen concentration of a gas according to the present invention.

The aforesaid phenomenon can be more clearly understood by analyzing the complex impedance characteristics of the oxygen concentration cell constituting the detector. More particularly, when the oxygen concentration detector of the invention is used to measure the oxygen concentration of the exhaust gas from an internal combustion engine, the oxygen concentration detector is required to withstand the high temperature of the exhaust gas and to show quick response even at a comparatively low temperature, so that the electrodes of the oxygen concentration detector are made of metals having a high catalytic activity and a high melting point, such as metals of the platinum group. The frequency characteristics of the impedance of the oxygen concentration detector for AC polarization is given by a complex impedance plot of $Z=Z'-jZ''$ as shown in FIG. 11. The complex impedance characteristics of FIG. 11 have two continuous semi-circular arcs, and an equivalent circuit of FIG. 12 gives a complex impedance characteristics substantially equivalent to those of FIG. 10.

Figure 12:
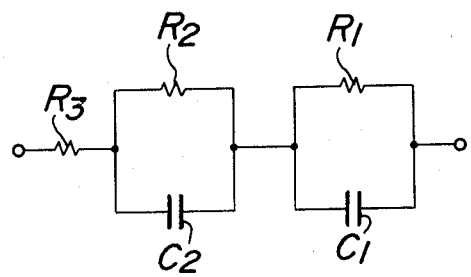
FIG. 12 is a diagram showing an equivalent circuit which provides the complex impedance characteristics of the oxygen concentration cell of FIG. 11.

In FIG. 12, $R_1$ corresponds to an electric resistance representing resistances of electrode reactions, $R_2$ corresponds to an electric resistance representing resistances at crystal boundaries in the solid electrolyte, $R_3$ corresponds to electric resistances of crystal grains in the solid electrolyte, $C_1$ corresponds to an electrostatic capacitance which is due to electrode reactions, and $C_2$ corresponds to an electrostatic capacitance which is due to capacitances of crystal boundaries in the solid electrolyte.

In FIG. 11, the resistance value of the point A corresponds to the sum of the three resistances of FIG. 12, i.e., $R_1+R_2+R_3$, the resistance value of the point B corresponds to the sum of $R_2+R_3$, and the resistance value of the point C corresponds to the resistance of $R_3$. The polarization of the oxygen concentration cell for the characteristic curve from the point A to the point B of FIG. 11 is mainly due to the resistance $R_1$ and the capacitance $C_1$, and that from the point B to the point C is mainly due to the resistances $R_2$, $R_3$ and the capacitance $C_2$. As regards the variation of the complex impedance characteristics with the frequency variation, the point A represents DC, and as the frequency increases, the complex impedance characteristics varies along the arcuate locus toward the point B and further along the other arcuate locus toward the point C.

The arcute characteristic from the point A to the point B of FIG. 11 varies considerably depending on the manner in which the electrodes are mounted on the solid electrolyte body and on the time length of using the oxygen concentration cell. Accordingly, if an AC voltage of a frequency range in the proximity of the point A is used, it is difficult to apply electric power necessary for the heating in a stable fashion, and high polarizing voltages are generated at the boundaries between the electrodes and the solid electrolyte which high polarizing voltages tend to cause chipping of the electrodes and deterioration of the solid electrolyte.

Besides, in the aforesaid frequency range, even a small difference of polarizing characteristics between the inner and outer electrodes causes a deviation of the DC component.

If an AC current of a frequency in the range from the point B to the point C flows through the oxygen concentration cell, even when the AC current is large enough for heating the solid electrolyte, no chipping of the electrodes and no deterioration of the solid electrolyte are caused and the DC component is not deviated. The reason for the elimination of the electrode chipping, the electrolyte deterioration, and the DC component deviation appears to be in that, when an AC voltage with a frequency higher than that of the point B is applied to the oxygen concentration cell, most of the polarization occurs in the solid electrolyte represented by the constants $R_2$, $C_2$, and $R_3$, and the polarization within the solid electrolyte is uniformly distributed in the direction of the thickness of the solid electrolyte, whereby chemical change or deterioration of the electrolyte due to electric current therethrough hardly occur. On the other hand, at the boundaries between the electrodes and the solid electrolyte represented by the constants $R_1$ and $C_1$ where the deterioration of the oxygen concentration cell normally occurs, polarization hardly occurs at the frequency above that of the point B, so that the boundaries are prevented from the aforementioned adverse effects. Stated otherwise, the AC voltage is applied at a frequency which is sufficiently high that the impedance between the electrodes to which the AC voltage is applied is largely independent of the interface capacitances between those electrodes and the surface of the solid electrolyte body.

Moreover, the arcuate locus from the point B to the point C is determined by the characteristics of the solid electrolyte per se, so that the locus is hardly affected by the manner in which the electrodes are mounted on the solid electrolyte and the change of the properties of the oxygen concentration cell with elapse of time. Accordingly, when an AC voltage in the frequency range between the point B and the point C is used, the impedance of the oxygen concentration cell becomes stable at a level corresponding to several percent to several tens percent of the DC resistance of the point A, so that stable heating of the solid electrolyte at a comparatively low voltage becomes possible.

Figure 13:
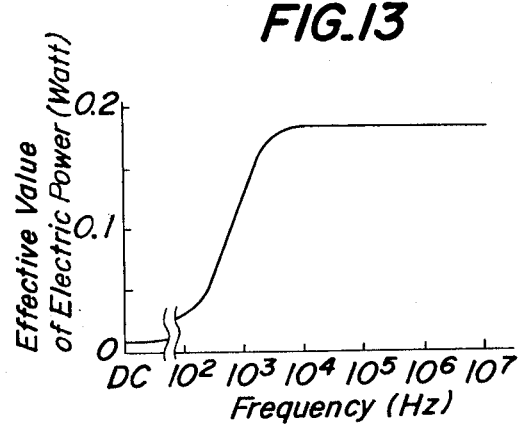
FIG. 13 is a graph showing the relationship between the frequency of an AC voltage and effective value of electric power.

In FIG. 13, an example of relationship between effective value of electric power consumed in the solid electrolyte and frequency of AC voltage applied on the detector is shown. In this case, the terminal voltage of the detector is kept at 30 V. When the applied voltage is DC, only small amount of current can flow, on the other hand sufficient amount of current to heat the detector can flow at high frequency.

More particularly, the value of the resistance $R_1$ normally increases rapidly with reduction of temperature, as compared with the resistances $R_2$ and $R_3$, so that the lower limit of the operative temperature of the oxygen concentration detector is restricted thereby. The present invention minimizes the effect of the resistance $R_1$ by applying an AC voltage whose frequency causes AC component polarization of the oxygen concentration cell mainly in the solid electrolyte thereof, i.e., an AC voltage with a frequency close to that of the point B or with a frequency on the arcuate locus between the point B and the point C, whereby the heating is effected by flowing the AC current through those resistances $R_2 + R_3$ or $R_3$ which are due to the polarization of the solid electrolyte irrespectively of the value of the resistance $R_1$.

It is noted that the impedance of the oxygen concentration cell assumes a minimum value at the point C, so that the heating can be effected from a lowest temperature by using the frequency of the point C.

The frequency between the point B and the point C varies depending on various factors such as the chemical composition, the temperature, and the shape of the solid electrolyte body, and the nature of the electrodes. For instance, in the case of an oxygen concentration cell formed by mounting platinum electrodes on opposite surfaces of a tubular ceramic body with one end thereof closed, which ceramic body has an outer diameter of 3.5 mm, and effective length of 10 mm, and a wall thickness of 0.75 mm, and consists of 95 mol% of zirconia ($ZrO_2$) containing 3% of clay and 5 mol% of yttria ($Y_2O_3$), the complex impedance of the oxygen concentration cell at 350° C. includes the point B of FIG. 11 at 100 Hz and the point C of FIG. 11 at a frequency higher than 10 kHz.

As regards the shape of the solid electrolyte body to be used in the oxygen concentration detector of the present invention, the tubular shape with the wall thickness at the closed tip thereof made thinnest as shown in FIG. 1 is preferable, because such shape results in a stable local heat generation. More particularly, in the solid electrolyte body of the preferred shape, the electric resistance per unit surface area becomes minimum at the tip portion thereof, so that when an AC voltage is applied to the oxygen concentration cell, the current is concentrated at the tip portion to selectively heat up the tip portion. Accordingly, it becomes sufficient to balance the electric power necessary for the heating with the heat dissipation from the tip portion, so that the operation of the tip portion of the solid electrolyte body can be ensured by supplying only a little electric power thereto, whereby a quick response can be achieved and the measurement can be effected with a sufficiently low impedance of the oxygen concentration detector even when the ambient temperature is comparatively low.

The invention will now be explained in further detail by referring to examples.

EXAMPLE 1

A tubular solid electrolyte body with a closed end having a tip outer diameter of 7 mm, a tip inner diameter of 5 mm, a middle portion outer diameter of 9 mm, and a middle portion inner diameter of 5 mm was prepared by using a zirconia ceramic consisting of 91 mol% of zirconia ($ZrO_2$) and 9 mol% of yttria ($Y_2O_3$). Platinum electrodes were applied to the inner and outer surfaces of the tubular solid electrolyte body as shown in FIG. 5. A porous spinel layer was applied to the outer electrodes on the outer surface of the solid electrolyte body by plasma jet spraying, so as to form an oxygen concentration detecting element. An oxygen concentration detector according to the present invention was completed by airtightly sealing the aforesaid element in a metal housing as shown in FIG. 1, wherein the pair of electrodes forming an oxygen concentration cell were used as electrodes for applying an AC voltage. The oxygen concentration detector thus completed was inserted into the exhaust gas of 315° C. from a gasoline engine. An AC voltage of 100 kHz and 100 V was applied to the oxygen concentration detector by using an electric circuit of FIG. 8 to generate heat in the solid electrolyte body, and various measurements were taken, such as the exhaust gas temperature and the response time of the detector. Similar measurements were taken on a conventional oxygen concentration detector without application of any AC voltage. The results are shown in Table 1.

The results of the measurements on the oxygen concentration detector of the invention refer to the data which were taken 3 minutes after applying the AC voltage thereto, and the effective value of electric power at that time was 0.5 W. In Table 1, the response time refers to the time necessary for the potential difference across the electrodes to change from 0.6 V to 0.3 V when the air/fuel equivalence ratio $\lambda$ of the exhaust gas is changed from $\lambda=1.1$ to $\lambda=0.9$.

TABLE 1

| Item | Detector of invention | Conventional detector | Reference detector |
| --- | --- | --- | --- |
| Exhaust gas temperature | 315° C. | 315° C. | 360° C. |
| AC voltage applied | 100 kHz 100 V | None | None |
| Temperature at inside of tip portion of oxygen detecting element | 350° C. | 305° C. | 350° C. |
| Electric resistance of oxygen detecting element | 25 KΩ | 105 KΩ | 21 KΩ |
| Response time | 0.15 sec | 1.0 sec | 0.15 sec |

As can be seen from Table 1, it was confirmed that the oxygen concentration detector according to the present invention had a very fast response even when the temperature of the gas being detected is low.

EXAMPLE 2

A tubular solid electrolyte body with a closed end having a tip outer diameter of 3 mm, a tip inner diameter of 2 mm, a middle portion outer diameter of 5 mm, and a middle portion inner diameter of 2.5 mm was prepared by using a zirconia ceramic consisting of 95 mol% of zirconia ($ZrO_2$) and 5 mol% of yttria ($Y_2O_3$). An inner electrode 2, outer electrodes 3, and AC electrodes 4 were mounted on the tubular solid electrolyte body in the manner as shown in FIG. 1, and a spinel porous layer was applied to the outer surface of the solid electrolyte body by plasma jet spraying after mounting the electrodes thereon. Thereafter, an oxygen concentration detector was assembled as shown in FIG. 1.

Figure 14:
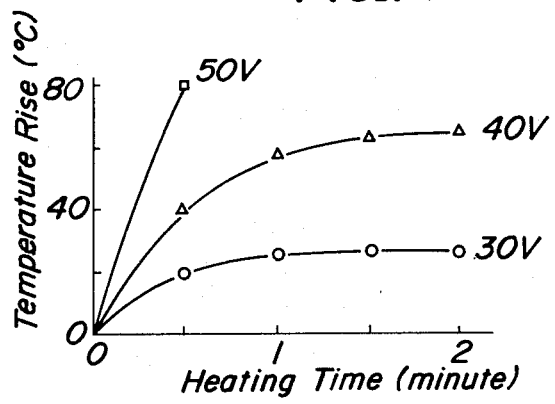
FIG. 14 is a graph showing the relationship between heating time and temperature rise with the AC voltage level at a high frequency as a parameter.

The oxygen concentration detector thus assembled was inserted in the exhaust gas of 300° C. from a gasoline engine, and a high-frequency voltage of 10 kHz was applied to the detector by using the electric circuit of FIG. 10. The temperature increase of the oxygen concentration detector was measured at different voltage levels of 30, 40 and 50 V. The results of the measurements are shown in FIG. 14. It was confirmed from the results of FIG. 14 that as the voltage applied to the AC electrodes increased, the heat generation in the solid electrolyte body increased and the temperature thereof became higher.

EXAMPLE 3

A tubular solid electrolyte body with a closed end having a tip outer diameter of 3.5 mm, a tip inner diameter of 2 mm, a middle portion outer diameter of 5 mm, and a middle portion inner diameter of 2.5 mm was prepared by using a zirconia ceramic consisting of 95 mol% of zirconia ($ZrO_2$), 5 mol% of yttria ($Y_2O_3$), and 3% by weight of clay. An inner electrode 2 and outer electrodes 3 were mounted on the solid electrode body as shown in FIG. 5, and a spinel porous layer was applied to the outer surface of the solid electrolyte body after mounting the electrodes thereon, so as to complete an oxygen concentration detector of the invention. The oxygen concentration detector thus completed was inserted in the exhaust gas of 300° C. from a gasoline engine, and voltages with frequencies higher than that of the point B of FIG. 11 were applied to the detector for generating heat in the solid electrolyte body. The result of the heat generation is shown in Table 2, in which heat generations in conventional detectors without applying any AC voltages and heat generation in reference cases with voltages of frequencies lower than that of the point B of FIG. 11 are shown for comparison. The complex impedance of the oxygen concentration detector of this Example at 350° C. was as shown in FIG. 11, and the frequency at the point B was 100 Hz and the frequency at the point C was higher than 10 kHz.

As described in the foregoing, according to the present invention, an AC electrode means to apply an AC voltage is mounted on an oxygen ion conductive solid electrolyte body, and an AC voltage, preferably an AC voltage with that frequency which causes most of the AC component polarization of the detector to be the polarization of the solid electrolyte body, is applied to the AC electrode means, so as to generate heat in the solid electrolyte body to keep the electrolyte at a high temperature. Using, the detector and the detecting method according to the present invention, even when the oxygen concentration detector is exposed to a gas of low temperature, the oxygen concentration of the gas is quickly and accurately detected in a stable manner with a low impedance and good response based on the principles of oxygen concentration cells. The oxygen concentration detector of the invention can be used to measure oxygen concentration in various kinds of exhaust gases, so that the invention contributes greatly to the art of energy saving and to the prevention of air pollution by exhaust gas.

TABLE 2(a)

| | | Initial conditions before voltage application | | | | Conditions of voltage application | | | | Characteristics during voltage application | | | |
| --- | --- | --- | --- | --- | --- | --- | --- | --- | --- | --- | --- | --- | --- |
| | | (1) | (2) | (3) | (4) | | | (5) | | (1) | (2) | (3) | (4) |
| Type | No. | Temperature (°C.) | Output (V) | Response (sec) | Resistance (Ω) | Frequency (Hz) | Voltage (V) | Polarization | Duration (hr) | Temperature (°C.) | Output (V) | Response (sec) | Resistance (Ω) |
| The invention | 1 | 300 | 0.98 | 1.0 | 60k | 100 | 45 | electrolyte | 24 | 350 | 0.96 | 0.1 | 26k |
| | 2 | 300 | 0.98 | 1.0 | 60k | 1k | 38 | electrolyte | 24 | 350 | 0.97 | 0.1 | 18k |
| | 3 | 300 | 0.98 | 1.0 | 60k | 10k | 26 | crystal grain | 24 | 350 | 0.97 | 0.1 | 18k |
| | 4 | 300 | 0.98 | 1.0 | 60k | 10k | 25 | crystal grain | 24 | 350 | 0.97 | 0.1 | 18k |
| | 5 | 300 | 0.98 | 1.0 | 60k | 10k | 26 | crystal grain | 2000 | 350 | 0.97 | 0.1 | 18k |
| | 6 | 300 | 0.98 | 1.0 | 60k | 10k | 26 | crystal grain | 0.05 | 350 | 0.97 | 0.1 | 18k |
| | 7 | 260 | 0.90 | 10 | 2M | 100k | 33 | crystal grain | 24 | 350 | 0.97 | 0.1 | 18k |

TABLE 2(a)-continued

| | | Initial conditions before voltage application | | | | Conditions of voltage application | | | | Characteristics during voltage application | | | |
|---|---|---|---|---|---|---|---|---|---|---|---|---|---|
| | | (1) | (2) | (3) | (4) | | | (5) | | (1) | (2) | (3) | (4) |
| Type | No. | Temperature (°C.) | Output (V) | Response (sec) | Resistance (Ω) | Frequency (Hz) | Voltage (V) | Polarization | Duration (hr) | Temperature (°C.) | Output (V) | Response (sec) | Resistance (Ω) |
| Prior art | 8 | 350 | 0.97 | 0.1 | 18k | — | — | — | — | — | — | — | — |

TABLE 2(b)

| | | Initial conditions before voltage application | | | | Conditions of voltage application | | | | Characteristics during voltage application | | | |
|---|---|---|---|---|---|---|---|---|---|---|---|---|---|
| | | (1) | (2) | (3) | (4) | | | (5) | | (1) | (2) | (3) | (4) |
| Type | No. | Temperature (°C.) | Output (V) | Response (sec) | Resistance (Ω) | Frequency (Hz) | Voltage (V) | Polarization | Duration (hr) | Temperature (°C.) | Output (V) | Response (sec) | Resistance (Ω) |
| Reference | 9 | 300 | 0.98 | 1.0 | 60k | 10 | 25 | electrode | 24 | 300 | 0.81 | 3.5 | 300k |
| | 10 | 300 | 0.98 | 1.0 | 60k | 10 | 50 | electrode | 24 | 300 | 0.60 | 8.2 | 800k |
| | 11 | 300 | 0.98 | 1.0 | 60k | DC | 25 | electrode | 24 | 300 | Crack and chip (6) | | |
| | 12 | 300 | 0.98 | 1.0 | 60k | DC | 50 | electrode | 24 | 300 | Crack and chip (6) | | |

Notes:
(1) Temperature measured at inside of tip of solid electrolyte body of oxygen concentration detector.
(2) Output in DC component of output voltage from oxygen concentration detector.
(3) Response in time for output to decrease from 0.6 V to 0.3 V when air/fuel equivalence ratio λ varied from 0.9 to 1.1.
(4) Resistance in DC resistance.
(5) Polarization column indicates that portion whose polarization assumes substantial part of voltage across terminals of oxygen concentration detector; wherein "electrolyte" refers to solid electrolyte body, "crystal grain" refers to crystal grains of solid electrolyte body, and "electrode" refers to electrode reactions.
(6) "Crack and chip" refer to cracking of solid electrolyte body and electrode chipping.

Although the invention has been described with a certain degree of particularly, it is understood that the present disclosure has been made only by way of example and that numerous changes in details of construction and the combination and arrangement of parts may be resorted to without departing from the scope of the invention as hereinafter claimed.

What is claimed is:

1. A method of detecting oxygen concentration in a gaseous environment using an oxygen concentration cell comprising the steps of:
preparing an oxygen ion conductive solid electrolyte body;
providing at least two separate electrodes contacting the oxygen ion conductive solid electrolyte body so as to form an oxygen concentration cell, at least one of said electrodes being exposed to a gaseous environment for detecting its oxygen concentration, and at least another one of said electrodes being exposed to a reference gaseous environment;
heating the solid electrolyte body by applying an AC voltage through at least two electrodes of said electrodes, and thereby decreasing the impedance of said cell, wherein said AC voltage is applied at a frequency which is sufficiently high that the impedance between said electrodes to which AC voltage is applied is largely independent of the interface capacitances between said electrodes to which AC voltage is applied and the surface of said solid electrolyte body; and
measuring the electromotive force of said cell when said solid electrolyte body is in its heated condition, said electromotive force representing, and thereby detecting the oxygen concentration in said gas.

2. A method of detecting oxygen concentration in a gaseous environment using an oxygen concentration cell comprising the steps of:
preparing an oxygen ion conductive solid electrolyte body;
providing a first set of at least two separate electrodes contacting the oxygen ion conductive solid electrolyte body so as to form an oxygen concentration cell, at least one of said electrodes being exposed to a gaseous environment the oxygen concentration of which is to be detected, and at least another one of said electrodes being exposed to a reference gaseous environment;
providing at least a third electrode separated from the electrodes of said first set, said third electrode contacting said solid electrolyte body;
heating said solid electrolyte body by applying an AC voltage through said third electrode and at least one of electrodes of said first set, thereby decreasing the impedance of said cell, wherein said AC voltage is applied at a frequency which is sufficiently high that the impedance between said electrodes to which AC voltage is applied is largely independent of the interface capacitances between electrodes to which AC voltage is applied and the surface of said solid electrolyte body; and
measuring the electromotive force of said cell when said solid electrolyte body is in its heated condition, said electromotive force representing and thereby detecting the oxygen concentration in said gas.

3. The method of claim 1 or 2 wherein the solid electrolyte body is heated to at least about 350° C. by application of the AC voltage.

4. The method of claim 1 or 2 wherein the solid electrolyte body has a tubular shape closed at one end and one of the two separate electrodes is on the inside of the tube and closed end, and the other of the two separate electrodes is on the outside of the tube and closed end.

5. The method of claim 1 or 2 further comprising preventing current due to said electromotive force from flowing into an AC voltage source.

6. An oxygen concentration detector for detecting the oxygen concentration in gases, comprising:
an oxygen ion conductive solid electrolyte body;

at least two separate electrodes contacting the solid electrolyte body so as to form an oxygen concentration cell;

AC power supplying means connected to at least two of said electrodes for heating said solid electrolyte body by applying an AC voltage, and thereby decreasing the impedance of said cell, wherein said AC power supplying means is arranged to supply an AC voltage at a frequency sufficiently high that the impedance between said electrodes to which AC voltage is applied is largely independent of the interface capacitances between said electrodes to which AC voltage is applied and the surface of said solid electrolyte body; and DC voltage detecting means connected to said electrodes constituting said oxygen concentration cell for measuring electromotive force of said cell when said solid electrolyte body is in its heated condition, said electromotive force representing and thereby detecting the oxygen concentration in gases.

7. An oxygen concentration detector for detecting the oxygen concentration in gases, comprising:

an oxygen ion conductive solid electrolyte body;

a first set of at least two separate electrodes contacting the solid electrolyte body so as to form an oxygen concentration cell;

at least a third electrode separated from the electrodes of said first set, said third electrode contacting the solid electrolyte body;

AC power supplying means connected to said third electrode and at least one electrode of said first set for heating the solid electrolyte body by applying an AC voltage, and thereby decreasing the impedance of said cell, wherein said AC power supplying means is arranged to supply an AC voltage at a frequency sufficiently high that the impedance between said electrodes to which AC voltage is applied is largely independent of the interface capacitances between electrodes to which AC voltage is applied and the surface of said solid electrolyte body; and DC voltage detecting means connected to said electrodes constituting said oxygen concentration cell for measuring electromotive force of said cell when said solid electrolyte body is in its heated condition, said electromotive force representing and thereby detecting the oxygen concentration in gases.

8. The detector of claim 7 wherein said third electrode is embedded within the solid electrolyte body.

9. The detector of claim 6 or 7, further comprising means for detecting selectively DC voltage level from terminal voltage of the detector, and means for preventing current due to DC voltage level of terminal voltage of the detector from flowing into the AC power supplying means.

10. The detector of claim 6 or 7, further comprising means for separating a circuit connected to the AC power supplying means from the terminal of the oxygen concentration detector.

11. The detector of claim 6 or 7, wherein said electrodes are made of metals of platinum group.

12. The detector of claim 6 or 7, wherein said electrodes are made of plantinum.

13. The detector of claim 6 or 7, wherein said electrolyte body has a tubular shape closed at one end.

* * * * *